United States Patent [19]
Bougamont et al.

[11] Patent Number: 5,651,359
[45] Date of Patent: Jul. 29, 1997

[54] DEVICE FOR INHALING POWDER

[75] Inventors: Jean-Louis Bougamont, Eu; David Leuliet, Mers les Bains; Hervé Lompech, Incheville, all of France

[73] Assignee: Sofab, France

[21] Appl. No.: 544,017

[22] Filed: Oct. 17, 1995

[30] Foreign Application Priority Data

Oct. 18, 1994 [FR] France ................................. 94 12399

[51] Int. Cl.⁶ .............................................. A61M 15/00
[52] U.S. Cl. ............................ 128/203.15; 128/203.21; 128/203.23
[58] Field of Search ...................... 128/200.24, 203.12, 128/203.15, 203.21, 203.23

[56] References Cited

U.S. PATENT DOCUMENTS

| | | | |
|---|---|---|---|
| 4,627,432 | 12/1986 | Newell et al. | 128/203.15 |
| 5,035,237 | 7/1991 | Newell et al. | 128/203.15 |
| 5,460,173 | 10/1995 | Mulhauser et al. | 128/203.15 |
| 5,492,112 | 2/1996 | Mecikalski et al. | 128/203.15 |
| 5,533,502 | 7/1996 | Piper | 128/203.21 |
| 5,562,918 | 10/1996 | Stimpson | 424/451 |

FOREIGN PATENT DOCUMENTS

| | | |
|---|---|---|
| 0 028162 | 6/1981 | European Pat. Off. . |
| 0 406 893 | 9/1991 | European Pat. Off. . |
| 2 662 936 | 12/1991 | France . |
| 89/02289 | 3/1989 | WIPO ....................... 128/203.21 |
| 91/02558 | 7/1991 | WIPO . |

*Primary Examiner*—Vincent Millin
*Assistant Examiner*—Eric P. Raciti
*Attorney, Agent, or Firm*—Bacon & Thomas

[57] ABSTRACT

A device for inhaling powder packaged in capsules, the device being of the type comprising a housing closed by a cover and containing means for supporting and transferring capsules, opening means for opening the capsules, a dispensing endpiece, and an air intake orifice. According to the invention, the means for supporting and transferring capsules are constituted by a moving charger provided with at least two chambers each designed to receive a respective capsule, and non-return means making it possible to use the cover to entrain the charger inside the housing in stepwise displacement in one direction only and to lock each chamber in succession in an inhalation position in which its capsule is in communication with the dispensing endpiece, and the opening means are constituted by two parallel blades respectively secured to the housing and to the cover and each adapted to cut off a respective one of the longitudinal ends of a capsule by successive displacements of the cover relative to the housing: firstly while entraining the charger in a first direction; and then on its own in the opposite direction after the charger has been locked in the inhalation position.

18 Claims, 4 Drawing Sheets

DEVICE FOR INHALING POWDER

The present invention relates to a device for inhaling powder, and more particularly powder that is packaged in capsules.

BACKGROUND OF THE INVENTION

Various substances, particularly medicines, need to be used and in particular inhaled in the form of a fine powder. A difficulty then arises of combining simplicity for the device, effectiveness, in particular accuracy and dispersion of the dose delivered, and safety, in particular hygiene and asepsis, etc. It therefore appears advantageous, a priori, to package such substances in single-dose capsules that then need to be opened, e.g. by being cut or perforated, prior to having their contents entrained in the inhaled flow of air. This difficult operation has already been performed in numerous different manners: thus, to expel the substance, proposals have been made to use: gravity or centrifuging; vibration or suction; or sweeping, either directly with the main flow, or else using flow induced by a venturi.

However, prior devices do not enable the creation or emission of the powder-carrying flow to be synchronized quickly with inhalation. In addition, those devices need to be refilled frequently, which makes them laborious to use.

OBJECT AND SUMMARY OF THE INVENTION

An object of the present invention is to solve those technical problems in satisfactory manner.

According to the invention, the object is achieved by means of a device for inhaling powder packaged in capsules, the device being of the type comprising a housing closed by a cover and containing means for supporting and transferring capsules, opening means for opening said capsules, a dispensing endpiece, and an air intake orifice, wherein said means for supporting and transferring capsules are constituted by a moving charger provided with at least two chambers each designed to receive a respective capsule, and non-return means making it possible to use the cover to entrain the charger inside the housing in stepwise displacement in one direction only and to lock each chamber in succession in an inhalation position in which its capsule is in communication with the dispensing endpiece, and wherein said opening means are constituted by two parallel blades respectively secured to the housing and to the cover and each adapted to cut off a respective one of the longitudinal ends of a capsule by successive displacements of the cover relative to the housing: firstly while entraining the charger in a first direction; and then on its own in the opposite direction after the charger has been locked in the inhalation position.

In an advantageous embodiment, said moving charger is a cylinder capable of revolving about a central axis and said non-return means are constituted by at least two pawls designed to co-operate with catches formed on the periphery of the housing and/or of the cover.

Preferably, the cover of the housing is cylindrical and has an axis of rotation that coincides with the central axis of the charger.

In which case, the free ends of the tabs of the pawls are situated on radii of the cylinder passing through the centers of the chambers.

According to an advantageous characteristic of the invention, the blades of the housing and of the cover are disposed at opposite ends of the chambers and include respective central orifices of a diameter slightly greater than that of the capsules and communicating respectively with the dispensing endpiece and with the air intake orifice in the inhalation position.

Preferably, the cover drives the charger by means of a free-wheel system.

In addition, said cover includes at least one peripheral projection slidably engaged in an interrupted groove formed in the periphery of the housing and against the ends of which the projection comes into abutment to limit the stroke of said cover relative to said housing.

The length of the peripheral groove of the housing corresponds to the distance between two chambers of the charger.

Also, provision is made for said pawls of the charger to be constituted by tabs extending substantially tangentially from the periphery of the charger and suitable for bending elastically on contact with the catches to pass over them.

According to another characteristic, the dispensing endpiece includes an internal exhaust duct that flares and that is closeable by means of a flap, and said air intake orifice is formed through the cover and is provided with a protective grid.

In a first variant embodiment, the housing includes a cup in which the charger is received.

When the charger is a rotary cylinder, the axis of said cup coincides with the central axis about which the cylinder revolves.

Optionally, said housing includes a opening facing one of the stop positions for the chambers of the charger to form a window for inspecting the filling level of said charger.

According to yet another characteristic, the chambers of the charger are shorter than the length of the capsules, and the cutting edges of the blades of the housing and of the cover are disposed in such a manner as to cut the capsules tangentially to their cylindrical side walls.

In another variant embodiment, the charger is a cylinder having seven chambers disposed on a circle, and seven corresponding peripheral pawls.

The present invention provides a pocket device that is easy to use since it prevents a double dose being issued and, while inhaling, it does not require any precise coordination between inspiration and a manual operation, while nevertheless protecting the user against accidental expiration.

The housing is provided with a dispensing endpiece such as an endpiece for suction via the mouth and it carries the mechanism enabling the substance to be dispensed.

The mechanism includes support and transfer means for bringing the capsules in turn into the inhalation position by a stepper movement achieved by stop members having deformable resilient supports and provided with non-return means for holding them in register with an exhaust orifice leading to the channel inside the above-mentioned endpiece; in principle this is done by means of a moving charger, e.g. one that revolves like a cylinder of a pistol, or one that can be displaced in linear manner being guided in a rectilinear housing. The capsules are placed therein either individually or while contained in packaging that is advantageously interchangeable, such as a strip or a disk which may optionally constitute the charger itself.

Thereafter, there are two cutting blades directed in the same direction along two opposite faces of the charger and spaced apart so that relative displacement thereof causes them to cut off both ends of a capsule at the moment it is put into the inhalation position in front of the exhaust orifice. To facilitate this operation, the edges of the cutting blades are advantageously oblique and they come into action in offset manner.

A drive member or driver, in theory non-reversible and under manual control, serves to move the charger successively from one stop position to the next. There is no need to use a transmission that provides mechanical advantage such as a worm screw or a Maltese cross; it is preferable to use the simple means of a free-wheel system moving back and forth between two abutments, and in particular a charger system having alternating locking, firstly in the go direction relative to a driver having a control knob on the same axis, and then relative to the housing during the return of the driver, optionally with assistance from a spring: to fasten the two members together, it would be possible to use ball ratchets, however it is preferable merely to use pawls operating in the same direction on two parallel paths; where appropriate, the heel ends of the cutting blades themselves may perform this function.

The two blades are then preferably mounted one on the housing and the other on the driver, the first then acting during the advance movement during which the driver drives the charger, and the second during the return movement during which the driver returns on its own to its starting position. The two pieces of scrap cut off the capsule are advantageously directed towards an internal receptacle.

BRIEF DESCRIPTION OF THE DRAWINGS

The invention will be better understood on reading the following description of a particular embodiment given with reference to the accompanying drawings, in which.

MORE DETAILED DESCRIPTION

Figure 1A:
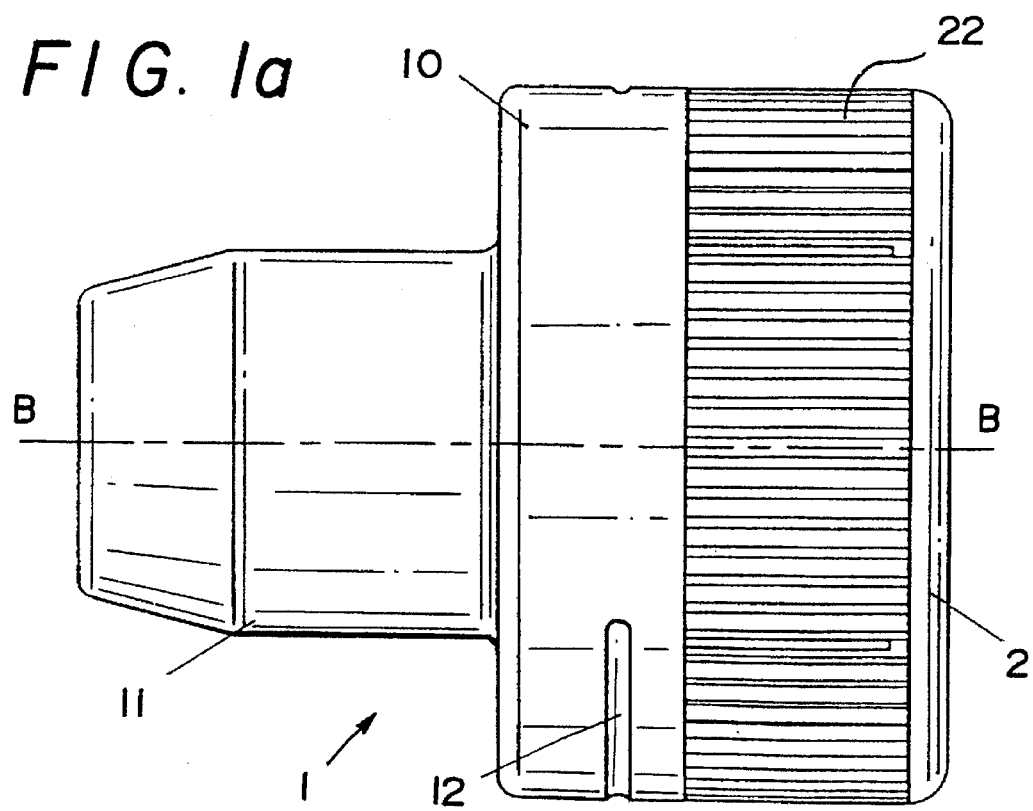
FIGS. 1a and 1b are outside views of the device of the invention as a whole, respectively when assembled and when disassembled.
Figure 1B:
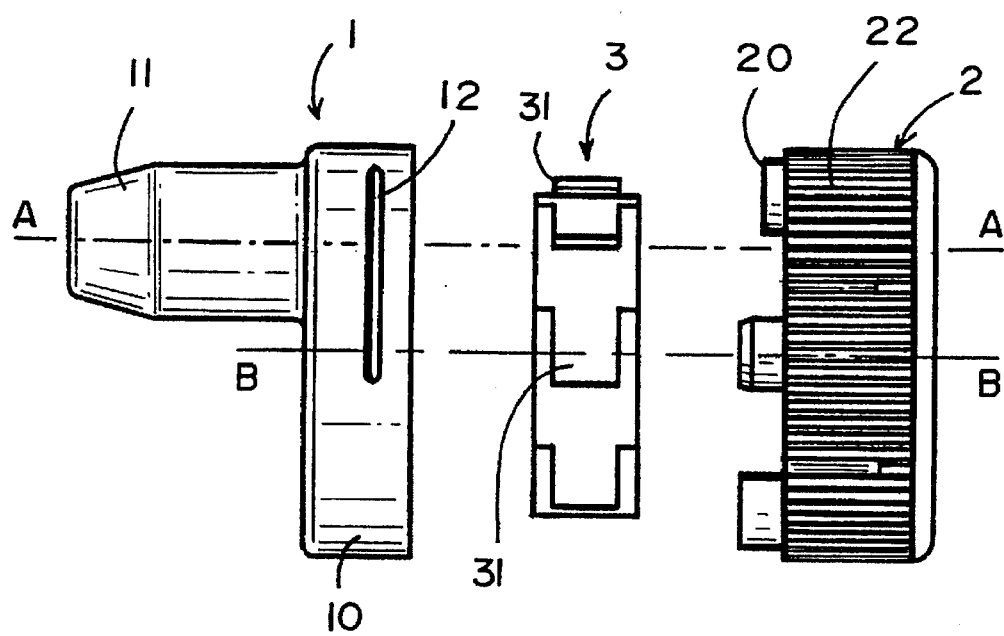

The inhalation device shown in FIGS. 1a and 1b comprises a housing 1 constituted in particular by a circular cup 10 about an axis B and carrying a dispensing endpiece 11 about an axis A, and a cylindrical cover 2 that closes the housing 1 engaging the cup 10 so as to rotate about the axis B. The dispensing endpiece 11 has an internal exhaust duct 11a that flares and that is closeable by a pivoting flap 5.

The cover 2 includes at least one peripheral retaining projection that is engaged in slidable manner in an interrupted groove 12 formed around the perimeter of the cup 10 of the housing 1. The projection 20 comes into abutment against the ends of the groove 12 to limit the rotary stroke of the cover 2 relative to the housing 1.

The cover 2 also includes an air intake orifice 21 (see FIG. 2) which is situated in the inhalation position in line with the axis A of the dispensing endpiece 11.

The air intake orifice is fitted with a protective grid 24.

The side face of the cover 2 is provided with fluting 22 making it easier to hold.

The housing 1 and the cover 2 enclose means for supporting and transferring capsules of powder.

Figure 2:
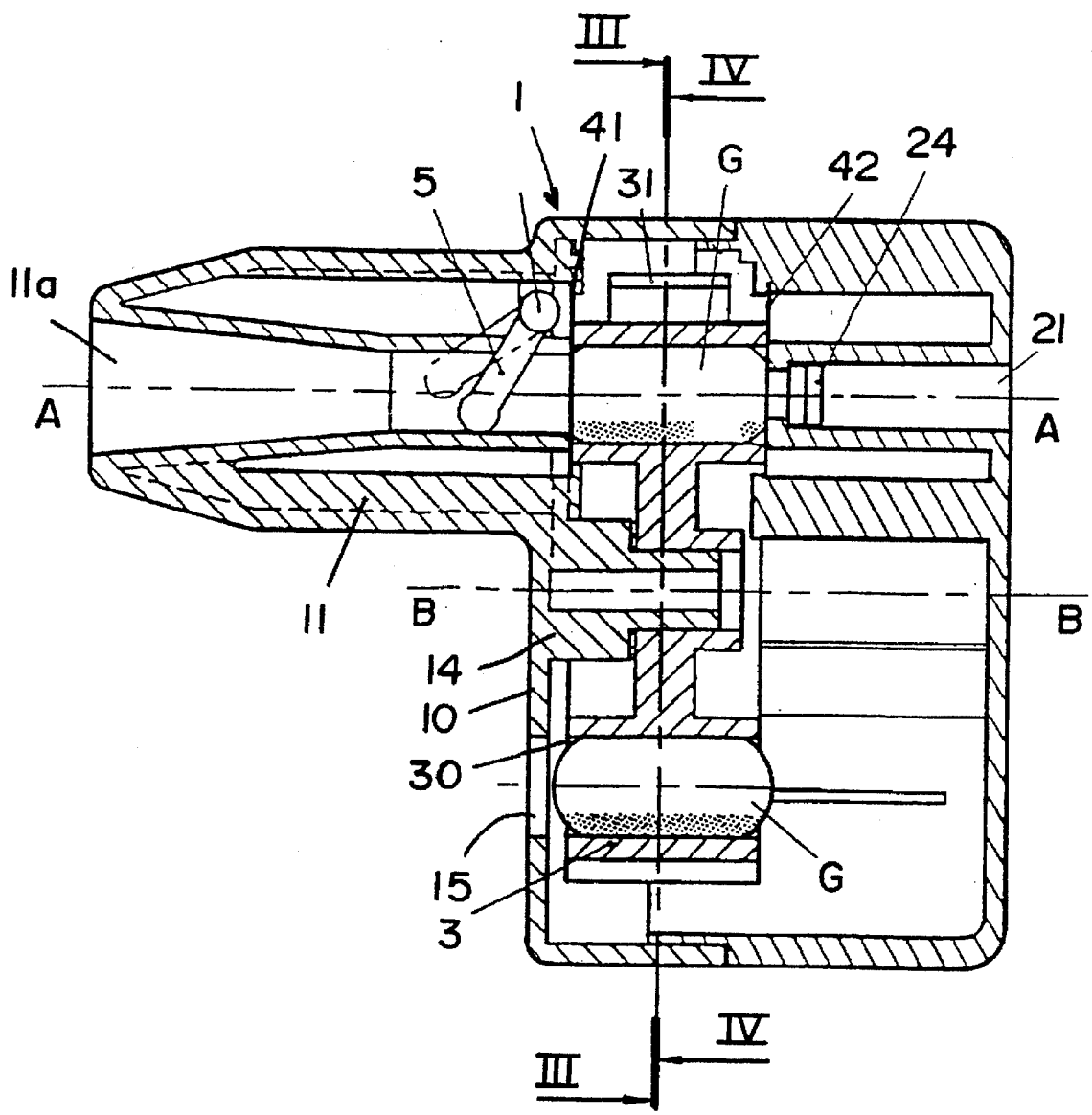
FIG. 2 is a longitudinal section view on line I—I showing the device of the invention.
Figure 3A:
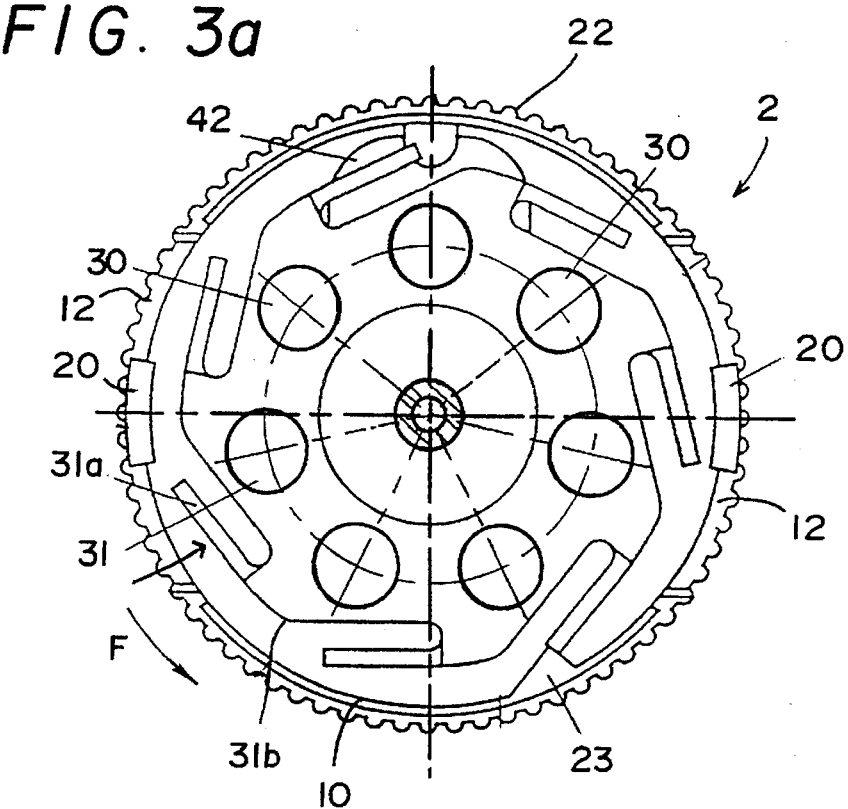
FIGS. 3a and 3b are cross-section views on III—III through the FIG. 2 device respectively with and without the charger.
Figure 3B:
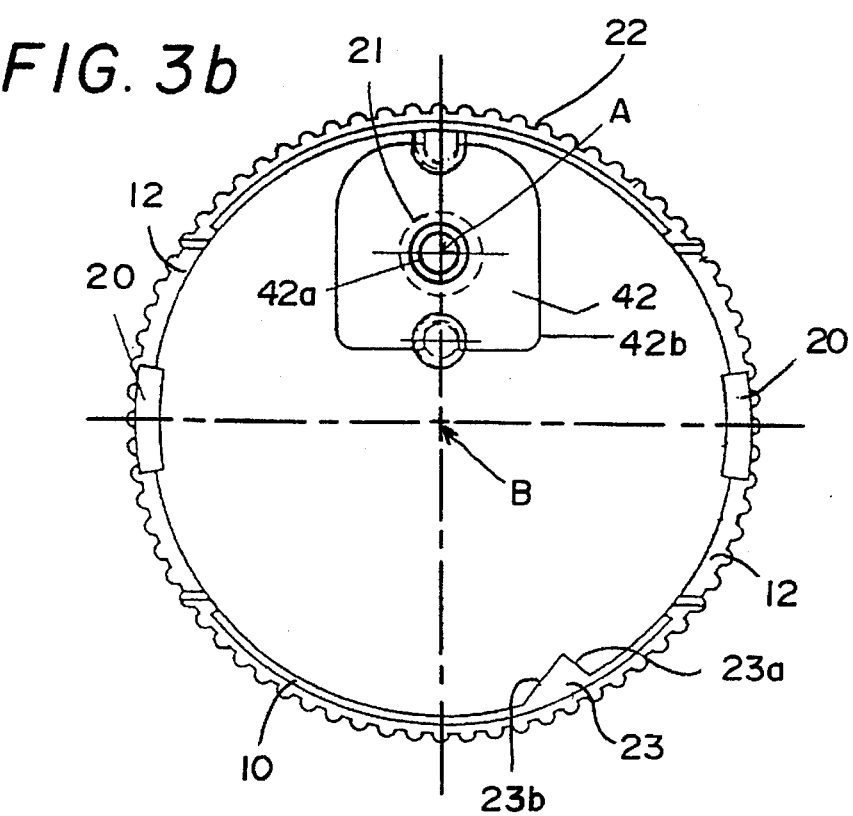
Figure 4A:
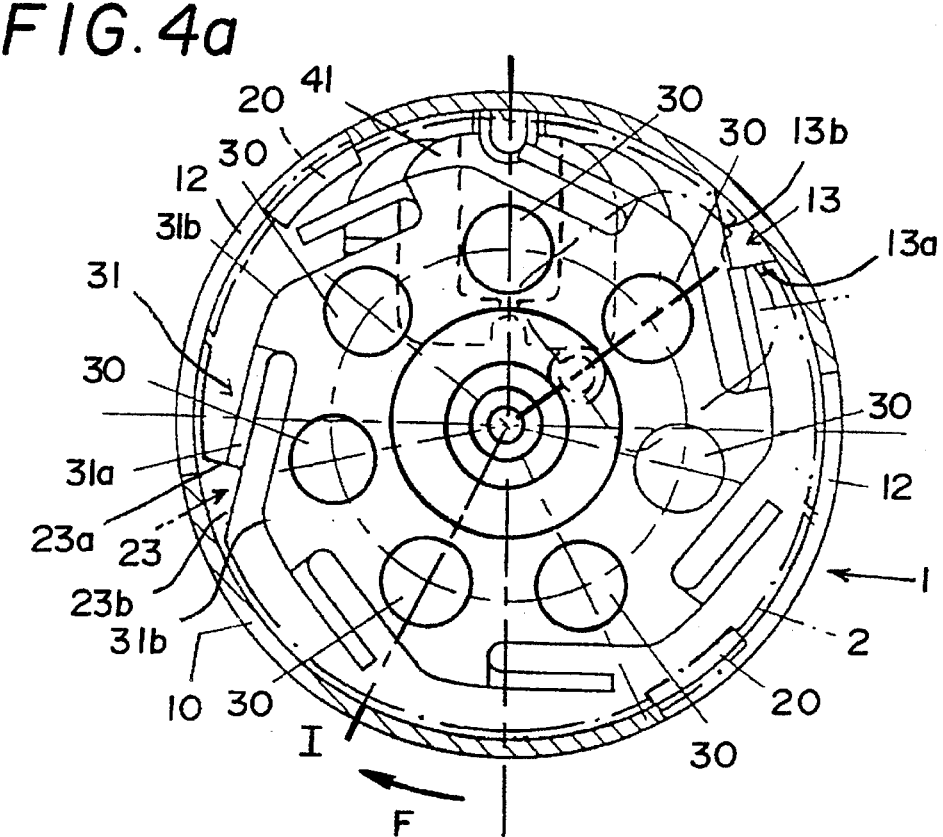
FIGS. 4a and 4b are cross-section views on IV—IV through the FIG. 2 device respectively with and without the charger.
Figure 4B:
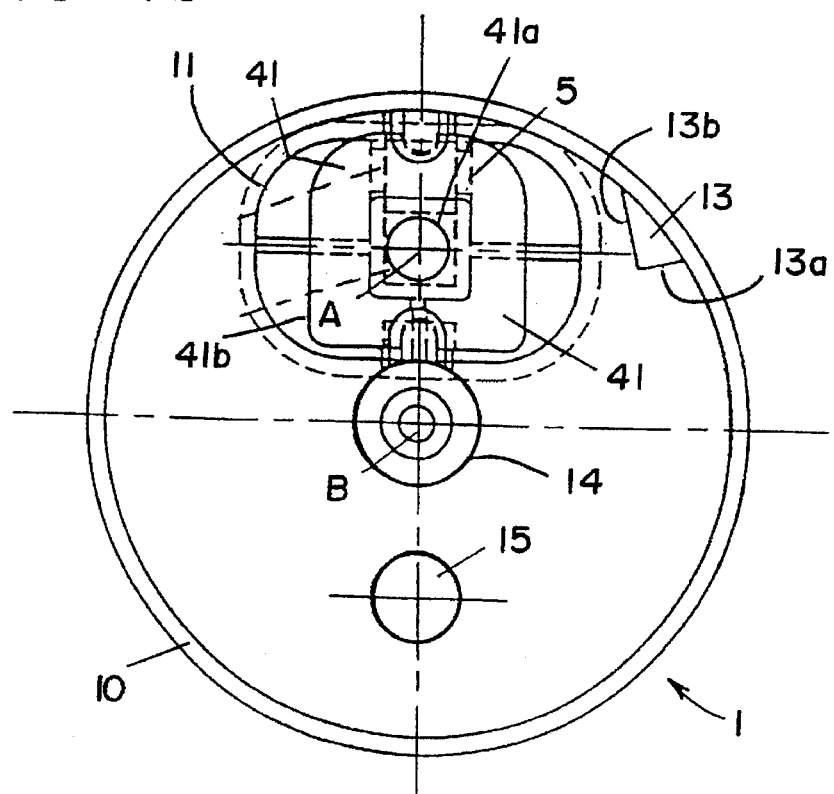

In the embodiment of FIGS. 1b and 2, these means are constituted by a charger 3 in the form of a cylinder that revolves about the central axis B, that is received in the cup 10, and that is provided with at least two chambers 30 each designed to receive a single capsule G containing a dose of medicine. The chambers 30 are slightly shorter in length than the capsules. In the embodiment of FIGS. 3a and 4a, the cylinder has seven chambers 30 disposed on a circular arc, and it is mounted on a stub axle 14 formed on the inside face of the cup 10.

The cylinder 3 also includes at least two peripheral pawls 31, and preferably seven pawls 31 corresponding to the chambers 30, as shown in FIGS. 3a and 4a.

The pawls 31 are designed to co-operate with catches 13, 23 formed around the housing 1 and/or the cover 2 to prevent the cylinder 3 from revolving in the direction opposite to arrow F, thereby forming a non-return system.

In other words, co-operation between the pawls 31 of the cylinder 3 and the catches 13, 23 makes it possible for the cylinder 30 to move angularly step by step and in one direction only inside the housing 1 under rotary drive from the cover 2. The cylinder 3 and the cover 2 are functionally interconnected by a free-wheel drive system allowing the cover 2 to return backwards relative to the arrow F towards its initial position after the cylinder 3 has been locked in place. This disposition thus serves to return the air intake orifice 21 so as to bring it in line with the axis A of the dispensing endpiece 11 for inhalation.

This angular displacement defines as many stop positions for the cylinder 3 as there are pawls 31 and causes each chamber 30 in succession together with the capsule G it contains to be brought to rest longitudinally in the inhalation position, i.e. on the axis A of the dispensing endpiece 11.

The cylinder 3 is locked in the inhalation position by the particular shapes of the pawls 31 and of the catches 13, 23.

The pawls 31 are constituted by tabs 31b extending substantially tangentially from the periphery of the cylinder 3 and capable of bending resiliently towards the central axis B on making contact with the catches 13, 23 so as to pass over them. The tabs 31a are extended forwards, relative to arrow F, by angled edges 31b. The free ends of the tabs 31a lie on radii of the cylinder 3 passing through the centers of the corresponding chambers 30.

The catches 13, 23 are constituted by triangular section lugs projecting towards the axis B.

The front side faces 13a, 23a of the catches 13, 23 in the forwards direction F form stop abutments for the free ends of the tabs 31a while their rear side faces 13b, 23b come to bear during rotation of the cylinder 3 firstly against the angled edges 31b of the pawls 31 and then against the tabs 31a. The join between the front faces 13a, 23a and the rear faces 13b, 23b of the catches forms an angle of about 90°.

Rotation of the cover 2 entraining the cylinder 3 thus gives rise, by a camming effect, to continuous and increasing elastic deformation of the tabs 31a in contact with the rear faces 13b, 23b of the catches 13, 23.

Continuing rotation causes the tabs 31a to pass over the angled joins between the front and rear faces 13a, 23a; 13b, 23b of the catches, whereupon they snap back (position shown in chain-dotted lines in FIG. 4a).

The catches 13, 23 are diametrically offset so that they always co-operate with two different pawls 31. The rear faces 13b, 23b of the catches are rectilinearly in line with the tabs 31a when the tabs are in abutment against the front faces 13a, 23a of the catches.

Nevertheless, a small amount of clearance remains, allowing angular displacement without deformation about each stop position of the cylinder 3.

The length of the groove 12 in the cup 10 of the housing in which the retaining projection 20 of the cover 2 slides thus corresponds substantially to the angular distance between two chambers 30 or two tabs 31a of the cylinder 3. In the embodiment of the figures, the stroke of the projection corresponds to an angular displacement of about 60°.

The housing 1 and the cover 2 also contain means for opening the capsules G.

In the embodiment shown, these means are constituted by two parallel blades 41 and 42 secured respectively to the housing 1 and to the cover 2.

Each of the blades 41, 42 is adapted to cut off one of the longitudinal ends of a capsule G by successive rotations of the cover 2 relative to the housing 1, firstly in a first direction F while entraining the cylinder 3, and then on its own in the opposite direction after said cylinder has been locked in the inhalation position. The blades 41, 42 are preferably identical and are disposed symmetrically at either end of the chambers 30. They have respective central orifices 41a, 42a of a diameter that is slightly greater than the diameter of the capsules G so as to allow the contents thereof to be evacuated.

To this end, the respective axes of the orifices 41a, 42a in the blades 41, 42 are suitable, in the inhalation position, for coinciding with each other and with the axis A common to the dispensing endpiece 11 and to the air intake orifice 21. The cutting edges 41b, 42b of the blades 41, 42 are disposed so as to cut through the capsules G in turn perpendicular to their cylindrical side walls and flush with the ends of the chambers.

The scrap drops into empty spaces that exist behind the blades 41, 42.

A path is thus opened between the intake orifice 21 and the exhaust duct 11a at the inlet to the endpiece 11 thus allowing a flow of air to sweep out the powder directly when the patient sucks on the mouth endpiece.

Advantageously, the cup 10 of the housing 1 includes an opening 15 in its front face forming a window facing one of the stop positions of the chambers 30 of the cylinder 3 to enable its filling level to be inspected.

We claim:

1. A device for inhaling powder packaged in capsules, the device being of the type comprising a housing closed by a cover that is movable relative to the housing and containing means for supporting and transferring capsules, opening means for opening said capsules, a dispensing endpiece, and an air intake orifice, wherein said means for supporting and transferring capsules are constituted by a moving charger provided with at least two chambers each designed to receive a respective capsule, and non-return means making it possible to use the cover to entrain the charger inside the housing in stepwise displacement in one direction only and to lock each chamber in succession in an inhalation position in which its capsule is in communication with the dispensing endpiece, and wherein said opening means are constituted by two parallel blades respectively secured to the housing and to the cover and each adapted to cut off a respective one of the longitudinal ends of a capsule by successive displacements of the cover relative to the housing: firstly while entraining the charger in a first direction; and then on its own in the opposite direction after the charger has been locked in the inhalation position.

2. A device according to claim 1, wherein said moving charger is a cylinder capable of revolving about a central axis.

3. A device according to claim 1, wherein said non-return means are constituted by at least two pawls designed to co-operate with catches formed on the periphery of the housing and/or of the cover.

4. A device according to claim 1, wherein the blades of the housing and of the cover are disposed at opposite ends of the chambers and include respective central orifices of a diameter slightly greater than that of the capsules and communicating respectively with the dispensing endpiece and with the air intake orifice in the inhalation position.

5. A device according to claim 2, wherein the cover of the housing is cylindrical and has an axis of rotation that coincides with the central axis of the charger.

6. A device according to claim 1, wherein the charger and the cover are interconnected by a free-wheel drive system.

7. A device according to claim 1, wherein said cover includes at least one peripheral projection slidably engaged in an interrupted groove formed in the periphery of the housing and against the ends of which the projection comes into abutment to limit the stroke of said cover relative to said housing.

8. A device according to claim 1, wherein the dispensing endpiece includes an internal exhaust duct that flares and that is closeable by means of a flap.

9. A device according to claim 3, wherein said pawls of the charger are constituted by tabs extending substantially tangentially from the periphery of the charger and which are suitable for bending elastically on contact with the catches to pass over them.

10. A device according to claim 9, wherein said moving charger is a cylinder capable of revolving about a central axis and wherein the free ends of the tabs of the pawls are situated on radii of the cylinder passing through the centers of the chambers.

11. A device according to claim 7, wherein the length of the peripheral groove of the housing corresponds to the distance between two chambers of the charger.

12. A device according to claim 1, wherein said air intake orifice is formed through the cover and is provided with a protective grid.

13. A device according to claim 1, wherein the housing includes a cup in which the charger is received.

14. A device according to claim 13, wherein said moving charger is a cylinder capable of revolving about a central axis, and wherein the axis of said cup coincides with the central axis about which the cylinder revolves.

15. A device according to claim 1, wherein said housing includes a opening facing one of the stop positions for the chambers of the charger to form a window for inspecting the filling level of said charger.

16. A device according to claim 1, wherein the chambers of the charger are shorter than the length of the capsules.

17. A device according to claim 1, wherein the capsules have cylindrical side walls and edges of the blades of the housing and of the cover disposed in such a manner as to cut the capsules perpendicular to their cylindrical side walls.

18. A device according to claim 3, wherein said moving charger is a cylinder capable of revolving about a central axis, and wherein the charger has seven chambers disposed on a circle, and seven corresponding peripheral pawls.

* * * * *